United States Patent [19]

Aoki et al.

[11] Patent Number: 5,491,150
[45] Date of Patent: Feb. 13, 1996

[54] SUPPLEMENTARY THERPEUTIC AGENTS FOR THE TREATMENT OF IMMUNODEFICIENCY SYNDROME

[75] Inventors: Tadao Aoki, Nigata; Hideo Miyakoshi, Hachiohji, both of Japan

[73] Assignee: Ajinomoto Co., Inc., Tokyo, Japan

[21] Appl. No.: 187,017

[22] Filed: Jan. 27, 1994

[30] Foreign Application Priority Data

Jan. 27, 1993 [JP] Japan .................................. 5-029668
Dec. 27, 1993 [JP] Japan .................................. 5-346875

[51] Int. Cl.$^6$ ..................... A61K 37/02; A61K 31/195; A61K 31/22
[52] U.S. Cl. ............................. 514/310; 514/563
[58] Field of Search ....................... 514/310, 563

[56] References Cited

U.S. PATENT DOCUMENTS

| | | | |
|---|---|---|---|
| 3,952,115 | 4/1976 | Damico et al. | 426/590 |
| 4,724,239 | 2/1988 | Morgan | 514/563 |
| 4,827,016 | 5/1989 | Morgan | 560/16 |

FOREIGN PATENT DOCUMENTS

| | | |
|---|---|---|
| 0561408 | 9/1993 | European Pat. Off. |
| 3906671 | 9/1990 | Germany |
| Wo91/18594 | 12/1991 | WIPO |
| WO92/21368 | 12/1992 | WIPO |

OTHER PUBLICATIONS

Biol. Chem. Hoppe–Seyler, vol. 370, No. 2, Feb. 1989, pp. 101–108, H.–P. ECk, et al., "Low Concentrations of Acid–Soluble Thiol (Cysteine) in the Blood Plasma of HIV–1 Infected Patients".
Database WPI, Derwent Publications, AN 84–173727 & JP–A–59–95220, Jun. 1, 1984.
Database WPI, Derwent Publications, AN 88–025682 & JP–A–62 286923, Dec. 12, 1987.
Proceedings of the Seventh Symposium on Host Defense Mechanisms Against Cancer, Nakone, Nov. 8–10, 1985, pp. 221–229, Tetsuo Taguchi, et al., "Lentinan: An Overview of Experimental and Clinical Studies of its Action Against Cancer".
Clinical Research, vol. 40, No. 2, 1992, p. 246A, J. G. Thoene, "In Vitro Effectiveness of Aminothiols and Disulfides Against HIV–1".
VII International Conference on AIDS, Florence, Italy, Jun. 16–21, 1991, Abstract No. W.A. 1050, La Colla Paola, et al., "In Vitro Effects of N–Acetyl Cysteine (NAC), Alone or in Combination with AZT, on Cell Growth and HIV–1 Multiplication".
International Immunology, vol. 4, No. 1, 1992, pp. 7–13, H.–P. Eck, et al., "T4+ Cell Numbers are Correlated with Plasma Glutamate and Cystine Levels: Association of Hyperglutamataenia with Immunodeficiency in Diseases with Different Aetiologies".

*Primary Examiner*—Arthur C. Prescott
*Attorney, Agent, or Firm*—Oblon, Spivak, McClelland, Maier, & Neustadt

[57] ABSTRACT

A supplementary therapeutic agent for the treatment of immunodeficiency syndrome with reduced NK (natural killer) activity and an immunopotentiator preparation containing it are provided.

A supplementary therapeutic agent for immunopotentiation which comprises L-cysteine, L-cystine, or L-glutamine, or salts thereof and is used in combination with an immunopotentiator such as lentinan, OK-432, sizofiran or the like, and an immunopotentiator preparation containing the agent. This combination of agents is useful as a supplementary therapeutic agent for the treatment of an immunodeficiency, such as low NK activity syndrome, chronic fatigue syndrome, acquired immunodeficiency syndrome, or congenital immunodeficiency syndromes.

10 Claims, 2 Drawing Sheets

PLASMA LEVELS OF TOTAL AMINO ACIDS

PLASMA LEVELS OF ESSENTIAL AMINO ACIDS

PLASMA LEVELS OF L-GLUTAMINE

PLASMA LEVELS OF L-CYSTINE

SUPPLEMENTARY THERPEUTIC AGENTS FOR THE TREATMENT OF IMMUNODEFICIENCY SYNDROME

BACKGROUND OF THE INVENTION

1. Field of the Invention

The present invention relates to a supplementary therapeutic agent which is employed to improve the effects produced by an immunopotentiator. The invention also relates to a therapeutic agent for immunodeficiency syndromes, such as chronic fatigue syndrome, low NK (natural killer) syndrome, acquired immunodeficiency syndrome, or congenital immunodeficiency syndromes.

2. Discussion of the Background

Several therapeutic agents are available for the treatment of immunodeficiency syndromes such as chronic fatigue syndrome, low NK syndrome, acquired immunodeficiency syndrome or congenital immunodeficiency syndromes. These immunopotentiators include lentinan, OK-432 (a lyophilized preparation of a low virulent strain, Su of *Streptococcus hemolyticus*), sizofiran, etc. (New Journal of Japanese Medicine, No. 3212, Nov. 16, 1985). E.P. 0561408 A1 teaches the use of polysaccharides having β-1,3-glucoside such as sizofiran, lentinan for treatment of chronic fatigue syndrome. A potentiator for host defense mechanism using lentinan is described in proceedings of the Seventh symposium on Host Defense mechanisms against cancer, Hakone, Nov. 8–10, 1985 (p. 221-p. 229). Unfortunately, in patients with such syndromes for several years, the expected therapeutic effects of these immunopotentiators are not always produced when they are administered alone.

SUMMARY OF THE INVENTION

Accordingly, one object of the present invention is to provide a supplementary therapeutic agent for the treatment of immunodeficiency syndrome which can be co-administered with immunopotentiators so as to improve the therapeutic effect of the immunopotentiators. The present inventors have now found that this object can be achieved by administering L-glutamine, L-cysteine, or L-cystine to patients who are also receiving immunopotentiators.

The present invention also provides therapeutic agents for the treatment of immunodeficiency syndrome which contains L-cysteine, L-cystine, L-glutamine, or salts thereof and an immunopotentiator as effective ingredients.

BRIEF DESCRIPTION OF THE DRAWINGS

FIG. 1 depicts the levels of total amino acids.

FIG. 2 depicts the levels of the essential amino acids.

FIG. 3 depicts the levels of L-glutamine.

FIG. 4 depicts the levels of L-cystine.

DETAILED DESCRIPTION OF THE PREFERRED EMBODIMENTS

Figure 1:
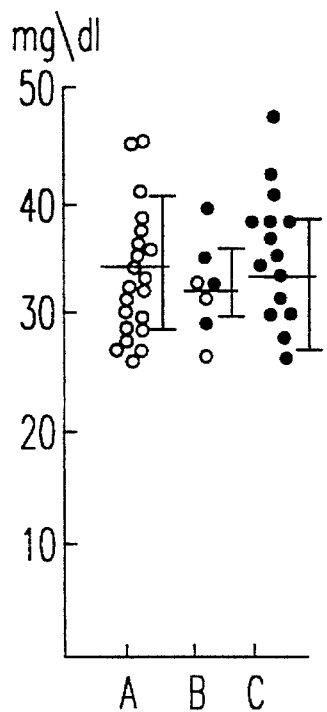
In FIGS. 1–4, plasma levels of the amino acids are plotted along the vertical axis. The plasma levels of amino acids in patients with immunodeficiency syndrome (A), that in the blood of patients with malaise and febricula but without immunodeficiency (B), and that in the blood of healthy persons (C) are plotted along the horizontal axis.

The present invention provides:

a supplementary therapeutic agent for the treatment of an immunodeficiency syndrome which contains L-cysteine, L-cystine, L-glutamine, or salts thereof as an effective ingredient; and a therapeutic agent for the treatment of an immunodeficiency syndrome which contains L-cysteine, L-cystine, L-glutamine, or salts thereof and an immunopotentiator as effective ingredients.

The supplemental therapeutic agents according to the present invention comprise L-cysteine, L-cystine, L-glutamine, or a mixture thereof. These amino acids are commonly available from a variety of commercial sources including Aldrich. Further, these amino acids are contained in native proteins and as such are commonly found in animals including humans. These amino acids can be administered without toxicity problems so long as excessive amounts are not administered.

The supplementary therapeutic agents described in the present invention can be prepared as dusting powders, powders, granules, tablets, sugar-coated tablets, capsules, solutions, etc. Suitable oral preparations contain 0.01-100% by weight, based on the total weight of the preparations, of L-cysteine, L-cystine, L-glutamine, or salts thereof. Alternatively, the supplementary therapeutic agents can be prepared as parenteral preparations such as suspensions, solutions, emulsions, ampules, and injections.

The dose of the supplementary therapeutic agents is 1–500 mg per day for adults in terms of the effective ingredients.

The therapeutic agents described in the present invention suitably comprise L-cysteine, L-cystine, L-glutamine or salts thereof and a therapeutic agent (immunopotentiator) for the treatment of immunodeficiency syndromes.

Suitable immunopotentiators useful in accordance with the present invention include lentinan, OK-432, or sizofiran. These immunopotentiators are commercially available and are currently used as antimalignant drugs.

The therapeutic agents are suitably presented as a parenteral injection. Lentinan and OK-432 can be administered intravenously, and sizofiran can be administered orally or intravenously.

The dose for adults is 1 to 500 mg per day in terms of the amino acids referred to above, and 1 to 20 mg per week, preferably 1 to 7 mg per week, in terms of the immunopotentiators, and they are mixed under these conditions for the administration.

EXAMPLES

Having generally described in this invention, a further understanding can be obtained by reference to certain specific examples which are provided herein for purposes of illustration only and are not intended to be limiting unless otherwise specified.

The present inventors have analyzed the amino acid levels in the periferal blood of patients with the syndromes for several years, who did not benefit from the therapeutic effects expected by the administration of immunopotentiators. As a result, they observed that the plasma levels of L-glutamine and L-cystine were lower in those patients than those in healthy persons.

Figure 2:
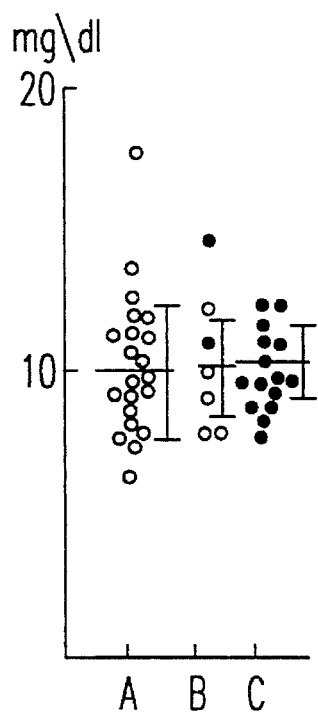
Figure 3:
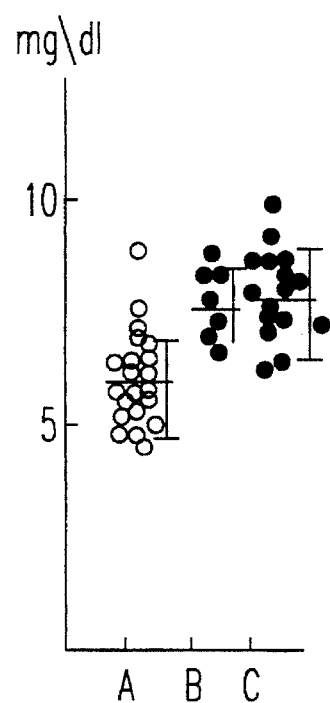
Figure 4:
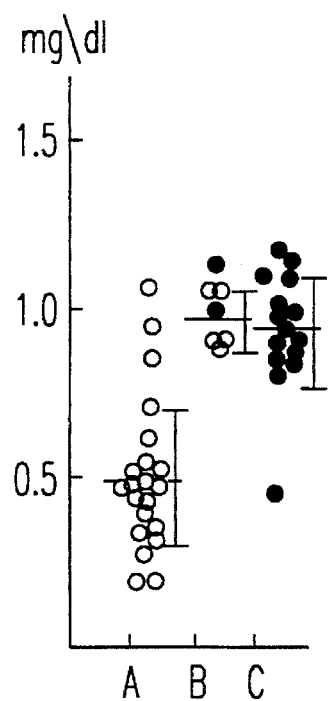

FIGS. 1–4 illustrate that patients with an immunodeficiency syndrome have lower plasma levels of L-glutamine and L-cystine as compared to those of healthy persons. In particular, the plasma levels of L-cystine in patients with an immunodeficiency syndrome are almost half those of the healthy persons.

On alternate days, L-cystine was administered to patients who had no improvement of clinical symptoms or signs upon the administration of therapeutic agents (immunopotentiators) alone. These patients with immunodeficiency syndromes with reduced NK activity, a majority of these patients had suffered from said syndromes for 5 or more years. It was found that administration of L-cystine over a period of several months contributed to the improvement of the clinical symptoms or signs and to the normalization of immunity.

Example 1

A 58-year-old male patient with chronic fatigue syndrome having low NK activity, accompanied by (1) fever, (2) excessive systemic malaise or fatigue and (3) tinnitus over 10 or more years, had an NK activity of 18.7% (normal value: 33% or higher) when he was hospitalized 6 years after the onset of the illness. This patient was administered with 1 mg of immunopotentiator "lentinan" by intravenous drip infusion every other day for half a year or more. His symptoms or signs were alternately improving and deteriorating with only a slight improvement. His lowered NK activity showed a slight increase, but was not restored to the normal value.

The L-cystine level in the peripheral blood of this patient had been reduced to half of the normal value. Accordingly, 200 mg L-cystine was administered by intravenous drip infusion every other day to the patient who was receiving lentinan as before. One month thereafter the drip infusion was replaced by the oral administration of a capsule containing 400 mg L-cystine which was given on alternate days for 1 month. The clinical condition of the patient gradually improved and was accompanied by an increase in his NK activity to values of 22%, 24.9%, 40.9% and 39% as determined every week beginning 1 month after the initiation of the combined use of L-cystine with lentinan.

Suspension of the administrations of L-cystine and also of the immunopotentiator 2 weeks thereafter, however, led to a decrease in the NK activity to 23.3% 3 weeks later, and to a relapse into the aggravated clinical conditions.

On the basis of the afore-mentioned results, it is expected that chronic fatigue syndrome with low NK activity may be treated by the administration of both the above amino acid and immunopotentiator, even in an intermittent manner or in gradually decreased doses, but not with complete interruption of the administration of both.

The foregoing results show that the administration of an immunopotentiator in combination with L-cystine promoted the NK activity. However, neither improvement of the clinical symptoms nor increase in the NK activity was observed by the administration of L-cystine alone.

Example 2

Cultivation of human lymphocytes in test tubes with L-cystine or L-glutamine activated lymphocytes, suggesting that activation of NK cells in the patient was promoted with L-cystine or L-glutamine. Here, L-cysteine is easily oxidized to L-cystine in the blood circulation, and thus acts in the same manner as L-cystine.

Obviously, numerous modifications and variations of the present invention are possible in light of the above teachings. It is understood, therefore, that within the scope of the appended claims, the invention may be practiced, unless otherwise specifically described herein.

What is claimed as new and desired to be secured by letters patent of the United States is:

1. A supplementary therapeutic composition for treating a patient with an immunodeficiency syndrome comprising (1) at least one agent selected from the group consisting of L-cysteine, L-cystine, L-glutamine, or a salt thereof and (2) a pharmaceutically acceptable carrier.

2. The supplementary therapeutic composition according to claim 1, wherein said amount of said agent is sufficient to return said patient's natural killer activity to normal levels.

3. The supplementary therapeutic composition according to claim 2, wherein said amount of said agent is sufficient to return said patient's natural killer activity to 33% or higher.

4. The supplementary therapeutic composition according to claim 1, wherein said agent is cystine.

5. A therapeutic composition for treating a patient with an immunodeficiency syndrome comprising (1) an amount of at least one supplemental therapeutic agent selected from the group consisting of L-cysteine, L-cystine, L-glutamine, or a salt thereof suitable to return the natural killer activity of said patient to normal levels, (2) an effective amount of an immunopotentiator and (3) a pharmaceutically acceptable carrier.

6. The therapeutic composition according to claim 5, wherein said immunopotentiator is selected from the group consisting of lentinan, OK-432, which is a lyophilized preparation of a low virulent strain, Su, of *Streptococcus hemolyticus*, or sizofiran.

7. A method for increasing the natural killer activity in a patient in need thereof comprising administering (1) at least one immunopotentiator and (2) at least one supplemental therapeutic agent selected from the group consisting of L-cysteine, L-cystine, L-glutamine, or salts thereof.

8. The method according to claim 7, wherein said immunopotentiator and said supplementary therapeutic agent are administered in a single pharmaceutically acceptable composition.

9. The method according to claim 7, wherein said immunopotentiator and said supplementary therapeutic agent are administered in separate pharmaceutically acceptable compositions.

10. The method according to claim 7, wherein 1–20 mg of said immunopotentiator are administered per week and 1–500 mg of said supplementary therapeutic agent are administered per day.

* * * * *